(12) United States Patent
Yamashita

(10) Patent No.: US 8,908,832 B2
(45) Date of Patent: Dec. 9, 2014

(54) RADIOGRAPHIC APPARATUS AND METHOD FOR THE SAME

(71) Applicant: Noboru Yamashita, Kyoto (JP)

(72) Inventor: Noboru Yamashita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 165 days.

(21) Appl. No.: 13/793,986

(22) Filed: Mar. 11, 2013

(65) Prior Publication Data

US 2014/0254753 A1   Sep. 11, 2014

(51) Int. Cl.
*H05G 1/64* (2006.01)
*A61B 6/00* (2006.01)

(52) U.S. Cl.
CPC ............................... *A61B 6/54* (2013.01)
USPC ............................. 378/98.12; 378/62

(58) Field of Classification Search
CPC ................................................ H04N 3/1587
USPC ................................................ 378/98.12, 62
See application file for complete search history.

(56) References Cited

U.S. PATENT DOCUMENTS

| | | | | |
|---|---|---|---|---|
| 8,548,122 B2 * | 10/2013 | Hay et al. | ......... | 378/62 |
| 8,693,622 B2 * | 4/2014 | Graumann et al. | ......... | 378/19 |
| 2004/0114717 A1 * | 6/2004 | Kato | ......... | 378/62 |
| 2008/0152088 A1 * | 6/2008 | Wang et al. | ......... | 378/98.12 |

* cited by examiner

*Primary Examiner* — Hoon Song
(74) *Attorney, Agent, or Firm* — Andrew F. Young, Esq.; Lackenbach Siegel, LLP

(57) ABSTRACT

A radiographic apparatus detector and method therefore obtains an image having excellent recognition without the effect of body movement. A single composite image is generated by connecting strip images in the movement direction of a radiation emitter, which are extending in a direction orthogonal to an emitter movement direction. A flat panel detector (FPD) moves so that an incident radiation region in the FPD follows the shooting. A transmissive image with an improved visual recognition is obtained since shooting the strip image in the FPD is conducted by using an unused part.

20 Claims, 12 Drawing Sheets

PRIOR ART

PRIOR ART

US 8,908,832 B2

RADIOGRAPHIC APPARATUS AND METHOD FOR THE SAME

CROSS REFERENCE TO RELATED APPLICATIONS

This application relates to JP Ser. No. 2010-235517, filed Oct. 20, 2010 and published as JP Pub. No. 2012-085852 on May 10, 2012, the entire contents of which are incorporated herein fully by reference.

FIGURE SELECTED FOR PUBLICATION

FIG. 1 is selected for publication

BACKGROUND OF THE INVENTION

1. Field of the Invention

The present invention relates to a radiographic apparatus to conduct an imaging of a transmissive image of a subject by using radiation, and to conduct especially a slot radiography to obtain plural rectangular images, and to generate a single image by connecting the obtained images in a width side direction.

2. Description of the Related Art

Referring now to FIG. 11, a conventional radiographic apparatus to take an image of a subject M by radiation is equipped in a medical facility. Such radiographic apparatus 51 comprises a table 52 on which the subject is loaded, a radiation source 53 to irradiate a radiation, and a radiation detector 54. An image in which a transmissive image of the subject M appears based on the signal output from the radiation detector 54 is obtained.

Some of such radiographic apparatus have a constitution which eliminates an effect of scattered radiation to provide a clear image. A manner to take an image by using such radiographic apparatus is illustrated in FIG. 11. The radiation source 53 and the radiation detector 54 move in a length direction of the table 52 while keeping each other's positional relationship. Plural images are taken during this movement. One composite image can be generated by connecting these plural images.

On shooting, a broadening of radiation irradiated from the radiation source 53 is restricted in the length direction of the table. (Referring to FIG. 11) Accordingly, each image taken is a long thin strip image in a width direction of table 52. The region N (in FIG. 11) indicates a part of the incident radiation beam B in the radiation detector 54. This region N is a radiography shooting angle of the radiation detector 54 when a strip image is obtained.

On the other hand, when the radiation passes through a subject M, a part of radiation scatters in the body of the subject M and becomes a scattered radiation S. The scattered radiation S is a cause that leads to an unclear image. Accordingly, it is preferable that the scattered radiation S is eliminated during conducting radiography when an image is taken.

According to a conventional constitution, a turbulence production in an image due to a scattered radiation S is suppressed by repeatedly taking strip images T. Specifically, the scattered radiation occurs in the body of the subject M changes the direction of travel due to scattering. Accordingly, the scattered radiation S directs towards the radiation detector 54 while it is out of the direction of travel of X-ray beam B. Accordingly, the scattered radiation S is not incident in the region N that is a shooting angle when a strip image T is taken. Accordingly, as the scattered radiation S which is a cause to produce turbulence is not an incident radiation, the obtained strip image T is a clear image without an effect of the scattered radiation S.

Then, referring to FIG. 12, a conventional composite image incorporating the whole body image of the subject M can be generated by arraying sequentially obtained strip images T in the length direction of table 52 over time and in order of shooting time. Since this composite image has been generated from images taken over time with excluding a scattered radiation S, it is clear but with the detriment of time. If the body moves in the time the images is not clear.

A radiographic apparatus comprising a means to cut a shooting time by minimizing movement of radiation detector 54 has been provided nowadays. The shorter movement of the radiation detector 54 becomes shorter, within the shorter time frame, the strip images T can be taken continuously. Accordingly, the shooting can be completed without letting the body of the subject M move and thus no disarray of images at the connection point occurs when the strip images T are connected. Accordingly, a composite image having an excellent visual recognition can be generated by such radiographic apparatus. (Patent Document 1 WO 2010/050032), however the shooting time cannot be further decreased.

PRIOR ART DOCUMENTS

PATENT DOCUMENT PCT International Publication No. WO2010-050032

Accordingly, there is a need for an improved radiographic apparatus that addresses one of the detriments noted herein.

ASPECTS AND SUMMARY OF THE INVENTION

Problems to be Solved by the Invention

In response, it is now recognized that there are several problems to be addressed.

In view of the above, there are nevertheless the following problems to be solved. Specifically, according to the conventional constitution, it is a problem that the continuous shooting rate as for strip images cannot be increased further than now due to characteristics of radiation detector 54.

The conventional radiation detector 54 comprises an amorphous selenium layer to convert the incident radiation to a carrier pair. The radiation from the amorphous selenium layer is incident, and a carrier pair (an electric charge) occurs corresponding to the strength of the incident radiation. This electric charge is read out by a sensor of the radiation detector 54 and then erased from the amorphous selenium layer. Under this condition, the radiation detector 54 enters into a standby condition for the following incident radiation.

Almost all electric charges occurring in the amorphous selenium layer are read out by the sensor of radiation detector 54. However, detrimentally, a part of them still remains in the amorphous selenium layer without being ever read out. This remaining electric charge disturbs the following shooting. Specifically, the left-over electric charge during the last strip image shooting is read out during the following shooting of the strip image T and then the visual recognition of the strip image T becomes poor because the obtained strip image T is superimposed with the subject's image obtained during shooting of the last strip image T.

Therefore, according to the conventional constitution, the continuous shooting rate is to be suppressed to moderate such phenomenon. Specifically, once shooting the strip image T takes place, the following shooting of the strip image T is being suspended until the electric charge remaining in amorphous selenium layer attenuates enough. A shooting of the strip image T cannot be conducted during this suspension period.

According to the conventional manner in which a radiation source 53 and a radiation detector 54 are keeping each other's positional relationship during shooting, an incident radiation is always in the same place of the radiation detector 54 whenever and however many times the shooting of the strip image is conducted, and therefore, the above suspension time duration is needed every shooting of a strip image T.

According to the conventional manner, even if the movement of the radiation detector 54 is suppressed as much as possible, wherein a radiation source 53 and a radiation detector 54 are not keeping each other's positional relationship, such suspension time duration is mandatory. The position of the incident radiation on a shooting of strip image and the position of the following shooting of strip image in a radiation detector 54 likely overlap. It is due to the constitution to suppress the movement of a radiation detector 54 as much as possible in the above manner. A phenomenon in which a subject's image that should appear in the last strip image T appears in the following strip image T occurs, wherein and wherever the incident radiations in the radiation detector 54 overlap, and therefore even in this manner, the above suspension time duration is needed every shooting of a strip image.

If a suspension time duration is needed, all the longer time is needed to completely obtain a series of strip images T. Then, since the subject moves meanwhile, a composite image having high visual recognition cannot be obtained.

According to the conventional constitution, the shorter time applied to obtain a series of strip images T, the higher performance radiation detector 54 is required, and as results, the equipment cost increases.

Under these circumstances, the purpose of present invention is to provide a radiographic apparatus that can obtain an image having an excellent visual recognition without an effect of the subject's body movement by completing the shooting in a short period of time.

Means for Solving the Problem

The present invention comprises the following constituents to solve the above problem. Specifically, a radiographic apparatus according the present invention comprises; a radiation source to irradiate a radiation; a radiation source movement means to move the radiation source; a radiation source movement control means to control the radiation source movement means; a detection means to detect the irradiated radiation and to output a detection signal; a detector movement means to move the detection means; an image generation means to generate a strip image, extending toward an orthogonal direction to the movement direction of the radiation source, from the detection signal by irradiating the incident radiation in a part of the detection means and continuously shooting while moving the radiation source for the subject; and a composite image generation means to generate a single composite image by connecting strip images in the movement direction of the radiation source, which are output from the image generation means; and wherein a detector movement means shoots without overlapping the region where the incident radiation is in the detection means on shooting the strip images and the region where the following incident radiation is in the detection means on shooting the strip images, while the detection means for the radiation source is moving in the movement direction of the radiation source.

Operation and Effect of the Invention

According to one aspect of the present invention, the radiographic apparatus comprises a composite image generation means to generate a single composite image by connecting strip images, extending toward the orthogonal direction to the movement direction of a radiation source, in a movement direction of the radiation source. Accordingly, a transmissive image of a subject having an excellent visual recognition, in which the scattered radiation is erased, can be obtained. Then, according to the present invention, it is devised that the continuous shooting rate for strip images can be increased. Specifically, the shooting is conducted while the detection means is moving for the radiation source so that the region where the incident radiation in the detection means on shooting a strip image will not overlap the region of the incident radiation in the detection means on shooting the following strip image. Once a radiation is irradiated to the detection means, an immediate shooting by using the instant irradiated part cannot be conducted. In contrast, according to the present invention, a continuous shooting can be conducted while the detection means is moving for the radiation source. Accordingly, as a shooting of a strip image is conducted while using an unused part on shooting in the detection means, a time between shootings decreases and the shooting can be completed before the subject's body moves. Accordingly, the subject's images appearing in each strip can be connected with each other without out-of-alignment on generating a composite image so that a transmissive image having an excellent visual recognition can be obtained.

Further, according to the proposed radiographic apparatus, a region of an incident radiation in the detection means on shooting of the strip image is a region of the strip extending toward an orthogonal direction to the movement direction of the radiation source; and it is preferable that the strip region in the detection means arrays in the movement direction of the radiation source; a detector movement control means moves the detection means for the radiation source so that the incident radiation enters into the different strip region on every shootings of the strip image.

Operation and Effect

The proposed constitution illustrates a further specific constitution of a radiographic apparatus of the present invention. Specifically, according to the above constitution, a composite image can be generated by connecting plural strip images. This strip image is taken by using one of the strip regions of the detection means. Accordingly, it allows elements of the detection means used on shooting each strip image not to absolutely overlap.

Further, according to the proposed radiographic apparatus, it is further preferable that the detector movement control means reciprocates the detection means for the radiation source on shooting strip images.

Operation and Effect

The proposed constitution also illustrates a further specific constitution of a radiographic apparatus of the present invention. Specifically, according to the above constitution, a rate of continuous shooting can be further increased. After shooting a region located in the one end of the detection means, if the detection means for the radiation source is moved reversely to the other end in the opposite direction so that the shooting of strip image can be conducted in sequence, the shooting can be continued without waiting until the strip region in the one end of the detection means becomes ready for shooting.

In addition, according to the proposed radiographic apparatus, it is further preferable that the strip region used when the movement of the detection means for the radiation source is outward is different from the strip region used when the movement of the detection means for the radiation source is homeward.

Operation and Effect

The proposed constitution illustrates a further specific constitution of a radiographic apparatus of the present invention. Specifically, according to the proposed constitution, the strip image shooting is conducted by using the strip region for outward movement from the one end of the detection means to the other end when the detection means relative to the radiation source moves reciprocally (when the movement of the detection means is outward.) Also, according to the above constitution, when the detection means moves from the other end to the one end (the movement of the detection means is homeward), the strip image shooting is conducted by using the strip region for homeward movement. Given the same strip region is used for outward and homeward movements, this strip region should be used twice when the detection means relative to the radiation source moves outward and homeward. Then, the time period between shootings might be too short and, in this scenario, a waiting time emerges until the strip region becomes available. According to the proposed constitution, as the strip region is used only once for shooting when the detection means relative to the radiation source moves outward and homeward, the strip image shooting can be continued without setting a waiting time.

In addition, it is further preferable that the outward strip region and the homeward strip region are arrayed one after the other in the detection means.

Operation and Effect

The proposed constitution illustrates a further specific constitution of a radiographic apparatus of the present invention. Specifically, if the outward strip region and the homeward strip region are arrayed one after the other in the detection means, the effect of the present invention can be achieved by moving the detection means relative to the radiation source because the strip region is used alternatively thereby. The relative movement distance of the detection means relative to the radiation source is short so that the rate for the continuous strip image shooting can be further increased.

In addition, according to the proposed radiographic apparatus, it is further preferable that the detector movement control means moves the detection means so that an unused strip region for shooting can be used, and then, when all strip regions are used, it moves the detection means so that the strip region used for shooting at the beginning can be used for shooting.

Operation and Effect

The proposed constitution illustrates a further specific constitution of a radiographic apparatus of the present invention. Specifically, when all strip regions are used for the strip image shooting; if the strip region that is used at the earliest shooting, i.e. the longest time passed since the last shooting, is used for the shooting, the time between the previous shooting and the following shooting should be sufficiently-long so that the strip image shooting could be immediately conducted even without setting a waiting time.

In addition, according to the proposed radiographic apparatus, it is further preferable that a radiographic apparatus comprises a collimator which collimates a radiation beam irradiated from a radiation source so that it can be irradiated all over to strip regions of the detection means.

Operation and Effect

The proposed constitution illustrates a further specific constitution of a radiographic apparatus of the present invention. If the collimator is equipped, a radiation can be correctly irradiated only to a single strip region on shooting a strip image.

In addition, according to the proposed radiographic apparatus, it is further preferable that the detection means comprises a conversion layer to convert a radiation to an electric charge.

Operation and Effect

The proposed constitution illustrates a further specific constitution of a radiographic apparatus of the present invention. The conversion layer is operative to convert a radiation to an electric charge and has a property by which it takes time until the generated electric charge completely attenuates. The constitution of the present invention is suitable for a constitution having a detection means comprising such conversion layer.

Effect of the Invention

According to the present invention, a single composite image is generated by connecting strip images in the movement direction of the radiation source, which are extending toward an orthogonal direction to the movement direction of a radiation source. Then, while the detection means relative to the radiation source is moving, a shooting is conducted so that a region of incident radiation in the detection means on shooting a strip image and a region of the following incident radiation in the detection means on shooting a strip image do not overlap. Accordingly, a transmissive image having an excellent visual recognition can be obtained because the strip image shooting is conducted using an unused part during the shooting in the detection means.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
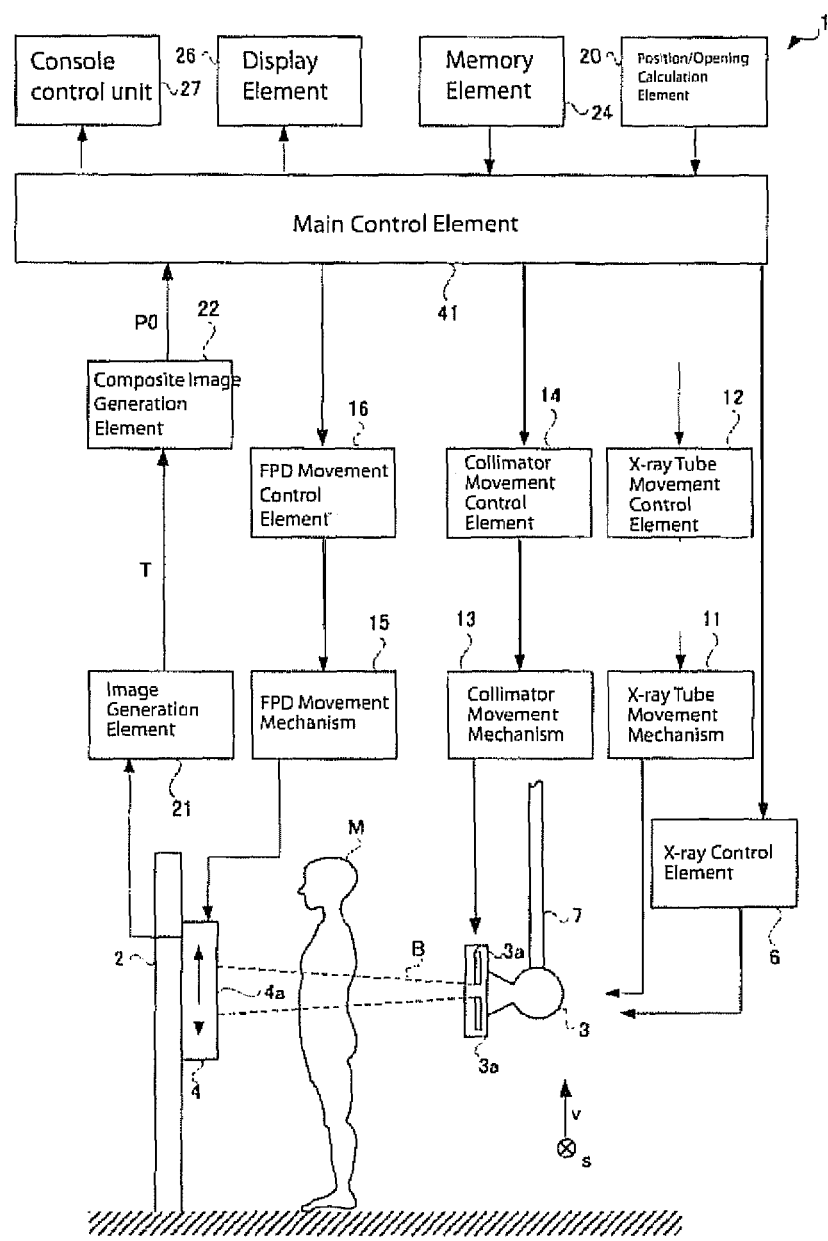
FIG. 1 is a block function diagram illustrating a radiographic apparatus according to Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple', 'connect', and similar terms do not necessarily denote direct and immediate connections, but also include connections through intermediate elements or devices. It will be understood, that suitable operable processor, processor controls, programming, electronic elements, memory devices and suitable sensors as needed for the proposed invention and method will be understood by those of skill in the art as being included herein. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent or that steps may not be replaced or that intermediate steps may not be conducted.

The present invention is now illustrated below in various non-limiting embodiments. According to an Embodiment, an X-ray corresponds to a radiation of the present invention, but other forms of radiation may be used without departing from the invention. In addition, FDP stands for Flat Panel Detector and will be understood as being operative by those of sufficient skill in the art.

Constitution of a Radiographic Apparatus

A constitution of a radiographic apparatus according to Embodiment 1 is first illustrated. Referring to FIG. 1, a radiographic apparatus 1 to shoot a standing subject M comprises a supporting stand 2 extending from a floor in a vertical direction V, an X-ray tube 3 to irradiate X-ray, a FPD 4 supported by the supporting stand 2, and a hanging supporting device 7 fixed on the ceiling and extending in a vertical direction V. The hanging supporting device 7 holds the X-ray tube 3 by hanging. The X-ray tube corresponds to a radiation source of the present invention and the FPD 4 corresponds to the detection means of the present invention.

During operation the FPD 4 can slide along the supporting stand 2 in the vertical direction V. Further, the hanging supporting device 7 is operably telescopic in the vertical direction V so that the position of the X-ray tube 3 in the vertical direction V can be changed along with a telescopic movement of the hanging supporting device 7. A vertical directional movement of the FPD 4 along the supporting stand 2 is conducted by a FPD movement mechanism 15 equipped between both 2, 4. This is controlled by a FPD movement control element 16. The FPD movement mechanism 15 corresponds to a detector movement means of the present invention and the FPD movement control element 16 corresponds to a detector movement control means of the present invention.

A movement of the X-ray tube 3 is illustrated. The movement of the X-ray tube can be conducted by an X-ray movement mechanism 11 set in the hanging supporting device 7. An X-ray tube movement control element 12 is equipped to control the X-ray tube movement mechanism 11. The X-ray tube 3 is moved by the X-ray tube movement mechanism 11; (1) in the vertical direction V, (2) in close or away direction relative to the FPD 4 and (3) in a horizontal direction S orthogonal to the direction from the X-ray tube 3 to the FPD 4 (the perpendicular direction to the paper plane in FIG. 1, or the direction along the side direction of the body of a subject M.) When the X-ray tube moves in the vertical direction, the hanging supporting device 7 thereof moves telescopically. The X-ray tube movement mechanism 11 corresponds to a radiation source movement means of the present invention and the X-ray tube movement control element 12 corresponds to a radiation source movement control means of the present invention.

The FPD 4 comprises a detection face 4a to detect an X-ray (referring to FIG. 1.) The detection face 4a is put upright in the vertical direction V in the radiographic apparatus 1. Accordingly, a shooting the standing subject M can be effectively and operably conducted. The detection face 4a is positioned to face the irradiation output of the X-ray tube 3. In other words, the detection face 4a is positioned along the plane made by two directions that are the horizontal direction S and the vertical direction V. Further, the detection face 4a is a rectangular, whereon the one side is in the horizontal direction S to which another side in the vertical direction V is orthogonal.

Figure 2:
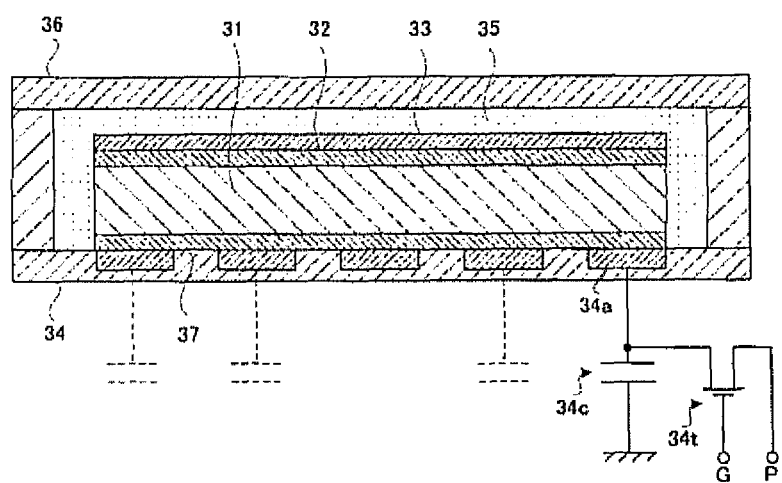
FIG. 2 is a partial cross sectional view illustrating a constitution of a Flat Panel Detector (FPD) according to Embodiment 1.

Referring to FIG. 2, a structure of a FPD 4 is illustrated. The FPD 4 is a direct conversion type X-ray detector to convert directly an X-ray to a carrier pair not via fluorescence. The FPD 4 comprises; an active matrix substrate board 34 that accumulates electric charges induced by transfer of a carrier and then reads out them; an amorphous selenium layer 31 that converts X-ray to a carrier pair (electric charge); a second high resistive film 32 for insulation; a common electrode 33 to put the amorphous selenium layer 31 into an electric field; an epoxy resin layer 35 for insulation; an auxiliary board 36 made of glass; and the first high resistive film 37 for insulation. Further, the FPD 4 has a layered constitution in which an active matrix substrate board 34, the first high resistive film 37, an amorphous selenium layer 31, the second high resistive film 32, a common electrode 33, an epoxy resin layer 35, and an auxiliary board 36 are layered in order. The amorphous layer 31 corresponds to a conversion layer of the present invention.

An amorphous selenium layer 31 is mode of highly-pure amorphous selenium of which the specific resistance is not smaller than $10^9$ Ωcm (preferably not smaller than $10^{11}$ Ωcm.) The thickness of the layer in the layering direction is in the range of 0.2 mm-3.0 mm. When an X-ray is irradiated to this amorphous selenium layer 31, a carrier pair that is a pair of an electron hole and an electron occurs. Since the amorphous selenium layer 31 is put into the strong electric field, a carrier moves alongside and an electric charge is induced into a collection electrode 34a formed on the active matrix substrate board 34.

A collection electrode 34a to collect carriers on the glass board is formed in the active matrix substrate board 34. The collection electrode 34a is contacting to the first resistive film 37 as well as arrayed two dimensionally on the surface of the active matrix substrate board 34. Referring to FIG. 2, the collection electrode 34a is connected to a condenser 34c to accumulate an electric charge. The electric charge collected at the collection electrode 34a is accumulated in the condenser 34c. The condenser 34c is connected to a transistor 34t. The transistor 34t comprises a gate G for electric current control and a read-out electrode P for reading out a detection signal, in addition to an input terminal connected to the condenser 34c. When the gate G of the transistor 34t is turned on, the electric charge accumulated in the condenser 34c flows to the read-out electrode P. Accordingly, the electric charge occurring in the amorphous selenium layer 31 is read out as an X-ray signal.

When an X-ray is irradiated to the amorphous selenium layer 31, a carrier pair inside the layer occurs. The carrier pair moves toward the common electrode 33 or the collection electrode 34a by the electric field generated by the common electrode 33 and transfers to outside of the layer. A part of electric charges remains in the amorphous selenium layer 31 without transferring. These electric charges will be remaining in the amorphous selenium layer 31 even after the detection signal is read out, and then will attenuate and annihilate over time. It takes 2 to 3 milliseconds after the X-ray irradiation until annihilation of the remained electric charge.

When the following X-ray transmissive shooting on continuous shooting of an X-ray shooting image is conducted while a carrier pair generated on the previous X-ray transmissive shooting has been remaining inside the amorphous selenium layer 31, a clear image cannot be obtained. Because, not only a carrier generated by the X-ray irradiation this time but also a carrier remained prior to the instant X-ray irradiation are collected at the collection electrode 34c, and as results, the last shot image appears in the obtained X-ray image as an virtual image. Accordingly, the following shooting cannot be conducted as long as a carrier pair remains in the amorphous selenium layer 31 after the X-ray irradiation.

Figure 3:
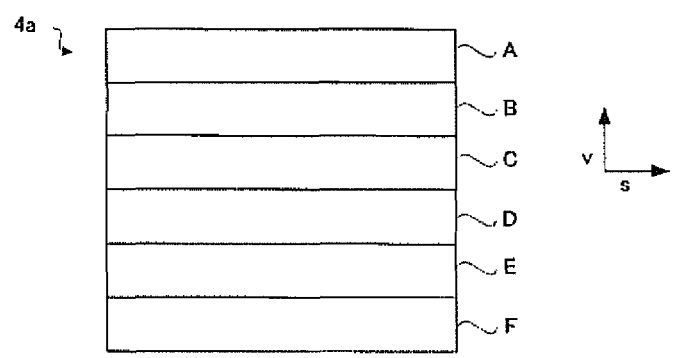
FIG. 3 is a plan view illustrating a constitution of a FPD according to Embodiment 1.

Referring to FIG. 3, a FPD 4 comprises plural strip regions A-F extending in a horizontal direction S orthogonal to a vertical direction V. For convenience sake, according to the present embodiment, a detection face 4a is illustrated as including 6 strip regions, but the practical FPD 4 includes approximately 30 strip regions, but is not limited thereto.

An X-ray tube control element 6 operatively controls a tube voltage of the X-ray tube 3, tube current and an irradiation time of X-ray. The X-ray tube control element 6 controls the X-ray tube 3 so that the X-ray tube 3 can radiate X-ray with a predetermined tube current, tube voltage and a pulse width. Parameters such as tube current are stored in a memory element 24.

A collimator 3a put in a radiographic apparatus 1 is illustrated. The collimator 3a, an annexed device of the X-ray tube 3, collimates the X-ray irradiated from the X-ray tube 3 to make a quadrangular pyramid shaped (cone shaped) X-ray beam B.

Figure 4:
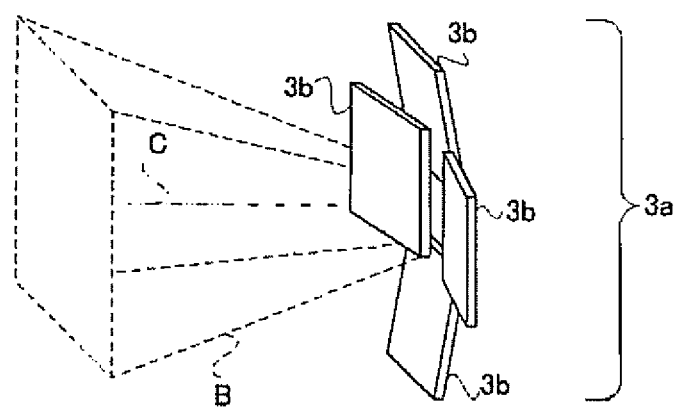
FIG. 4 is a perspective view illustrating a constitution of a collimator according to Embodiment 1.

The detail of the collimator 3a is illustrated. Referring to FIG. 4, the collimator 3a comprises one pair of leaves 3b that moves mirror-image-symmetrically on the basis of central axis C and another pair of leaves 3b that also moves mirror-image-symmetrically on the basis of central axis C. The collimator 3a moves the leaves 3b so that it not only allows the cone-shape X-ray beam B to be irradiated to a whole face of the detection face 4a of the FPD 4, but also, for example, allows the fan-shape X-ray beam B to be irradiated only to the center part of the FPD 4. The central axis C is also an axis specifying the center of the X-ray beam B. Further, one of the pairs of the leaves 3b adjusts broadening of the quadrangular pyramid shaped X-ray beam in the vertical direction V, and the other pair of the leaves 3b adjusts broadening of the X-ray beam in the horizontal direction S. A collimator movement mechanism 13 conducts the change of opening level of the collimator 3a. The collimator movement control element 14 controls the collimator movement mechanism 13. Further, a constitution allows the collimator 3a not to move mirror-image-symmetrically, but optionally may allow a pair of leaves 3b to move independently.

A position and opening level calculation element 20 operatively calculates an opening level of the collimator 3a, a position of the X-ray tube, an inclination dip of the X-ray tube 3, and a position of the FPD 4. Each control element 12, 14, 16, 18 controls each mechanism with calculation results related to the position and opening level that calculation element 20 calculates.

An image generation element 21 operatively generates a strip image T by combining the detection data output from the FPD 4, in which a projection image of the subject M appears. The strip image T is a strip-like image having the width side in the vertical direction V and the length side in the horizontal direction orthogonal to the vertical direction V. A composite image generation element 22 generates a single composite image PO by connecting plural strip images T in the vertical direction V thereof, in which the positions where the subject M is appeared are different. The connected composite image PO is displayed on the display element 26. The image generation element 21 corresponds to the image generation means of the present invention and the composite image generation element 22 corresponds to the composite image generation means of the present invention.

A console control unit 27 is set up for an operator to input each instruction, and a memory element 24 stores all kinds of parameters used for X-ray shooting, including such as control data of the X-ray tube 3, position data of the X-ray tube 3, the opening level of the collimator 3a, position data of the vertical direction V as to the FPD 4, and position data of the horizontal direction S as to the supporting stand 7. In addition, referring to FIG. 1, a radiographic apparatus 1 also operatively comprises a main control element 41 to controls integratively each element 6, 12, 14, 16, 18, 20, 21, 22, 24. The main control element 41 comprises CPU to run a variety of programs and operate a variety of electronic components thereby to activate each element. On the other hand, each element can be activated separately by an arithmetic device to run each element.

Operation of a Radiographic Apparatus 1

Figure 5:
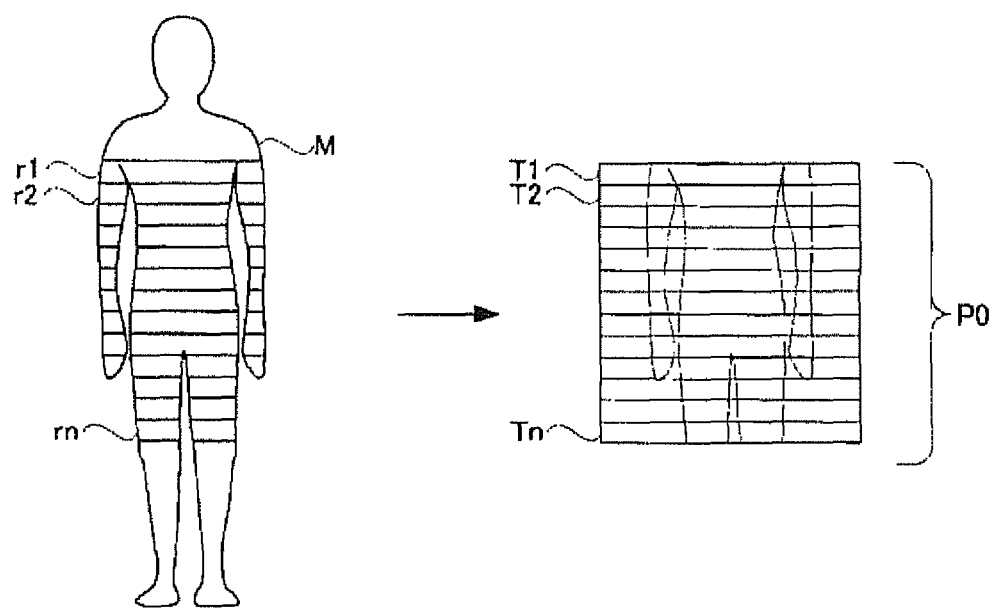
FIG. 5 is a pattern diagram illustrating an operation of a radiographic apparatus according to Embodiment 1.

Next, an exemplary operation of the radiographic apparatus 1 is illustrated. The illustration of the operation illustrates a manner in which plural strip images T having a rectangular shape of which the width side is in the vertical direction V are obtained and then a single composite image PO is generated by connecting these in the vertical direction V. Specifically, referring to FIG. 5, each region r1-rn of the subject M is shot n times to provide n number of strip images T1-Tn which will be connected in the vertical direction V to generate a composite image PO to be used for diagnoses according to the shooting operation of the radiographic apparatus, A composite image obtained in this manner is suitable because no scattered content is appeared.

Accordingly, a practical operation of the radiographic apparatus 1 conducts that when the target examination area of the subject M is split to each region r1-rn in the vertical direction V, the highest region r1 among the regions in the vertical direction V is shot first to take a strip image T1, and then the shooting position of a strip image T is lowered in sequence and the lowest region rn in the vertical direction V is shot at last.

A more specific operation of a radiographic apparatus 1 is illustrated.

Figure 6:
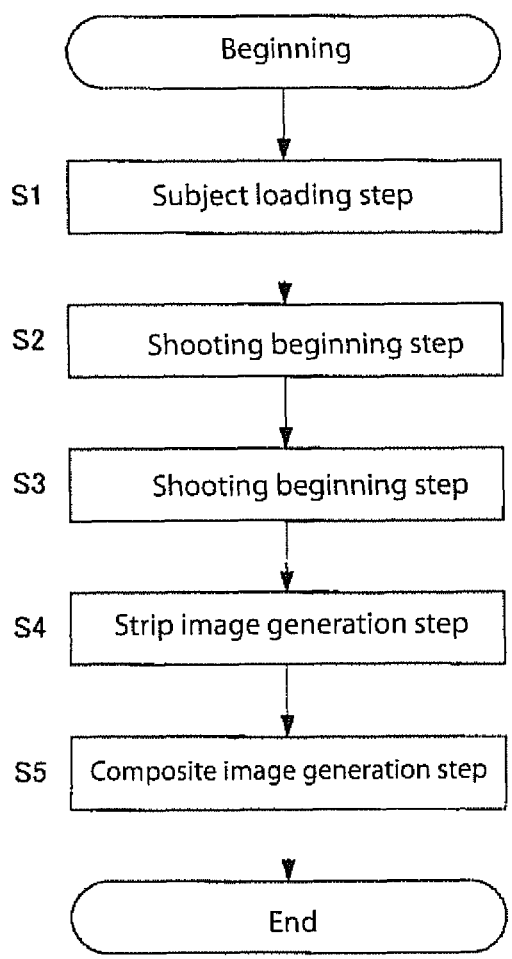
FIG. 6 is a flow-chart illustrating an operation of a radiographic apparatus according to Embodiment 1.

Referring to FIG. 6, when the subject M is shot by using a radiographic apparatus according to Embodiment 1, first the subject M is positioned in a shooting angle of the apparatus (Subject loading step S1) and then the instruction at beginning of shooting is given (Shooting beginning step S2.) And then movements of a X-ray tube 3 and a FPD 4 begin, shooting the strip image T begins (Shooting beginning step S3) and a trip image T is generated from the detection signals that the FPD 4 output (Strip image generation step S4.) At last, a composite image PO is generated based on the strip images T (Composite image generations step S5.) Each step is illustrated in order below.

Subject Loading Step S1 and Shooting Beginning Step S2

A subject M stands between an X-ray tube 3 and a FPD 4 prior to shooting. Thereby, the subject M is loaded on radiographic apparatus 1. Then, when an operator provides the radiographic apparatus 1 with an instruction to begin shooting through a console control unit 27, the X-ray tube 3 and the FPD 4 move in the vertical direction V in accordance with a control by a control element 12, 16 to control each movement. Then, the X-ray tube 3 and the FPD 4 move to the positions sandwiching a region r1, shown in FIG. 5, of the subject M (Referring to upper left in FIG. 7.)

A collimator movement control element 14 moves the leaves 3b of the collimator 3a so that a fan-like X-ray beam broadening in the horizontal direction S orthogonal to the vertical direction V rather than the vertical direction can be obtained. If the X-ray beam is irradiated under this condition, the X-ray beam is collimated and becomes an incident radiation in one of the strip regions that is a part of detection face 4a of the FDP 4. The X-ray tube 3 moves to the position, wherein the X-ray beam is incident in the region r1 of the subject M.

An operator instructs an X-ray irradiation through the console control unit 27 and the X-ray is irradiated from the X-ray tube. The X-ray beam is collimated by the collimator 3a at this time so that it becomes incident in the rectangular shaped region in the horizontal direction orthogonal to the vertical direction relative to the subject M (Referring to FIG. 5.)

Figure 7:
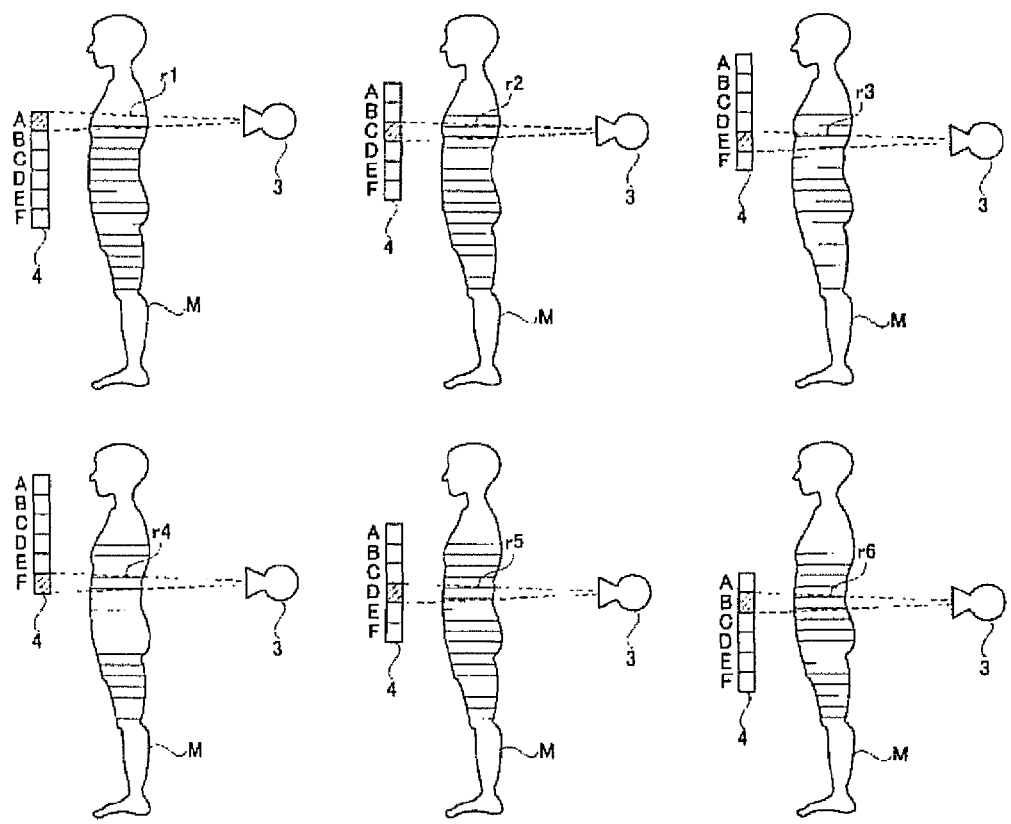
FIG. 7 is a pattern diagram illustrating an operation of a radiographic apparatus according to Embodiment 1.

The position of the FPD 4 is illustrated on shooting the region r1. At this time, the FPD 4, as shown in upper left of FIG. 7, is positioned wherein the incident X-ray beam is irradiated to the upper end in the vertical direction V of the FPD 4. The FPD 4 is split in the vertical direction by a width along the vertical direction of the incident X-ray beam to the FPD 4, whereby the FPD 4 is presumed as the rectangular regions A-F in the horizontal direction S orthogonal to the vertical direction V. (Referring to FIG. 3) And it is presumed that the FPD 4 can be split to 6 strip regions for convenient sake but is not limited thereto. Accordingly, as shown in the upper left of FIG. 7, the position of the FPD 4 on shooting the region r1 is the position where the X-ray beam is incident in the strip region A that is the upper end position of the FPD 4 in the vertical direction V.

The FPD 4 detects an X-ray at the strip region A and outputs the detection signal to an image generation element 21. Since a left-over electric charge without reading out remarkably remains in the amorphous selenium layer 31 in the strip region A right after output of the detection signal, the strip region A cannot be used for the next immediate shooting. On the other hand, no incident X-ray beam is yet in other strip region B-F of the FPD 4 and therefore no carrier remains so that they can be used for the next immediate shooting. Then, the strip region C is used for the next shooting.

After shooting the region r1 of the subject M, the X-ray tube and the FPD 4 move again, and then the radiographic apparatus 1 shoots this time the region 2 which is the lower adjacent region of the region r1. At this time, the X-ray tube moves to the position at which the collimated X-ray beam's is incident in the region r2 of the subject M.

The position of the FPD 4 is illustrated on shooting the region r2. As shown in the upper middle of FIG. 7, the FPD 4 moves this time to the position at which the X-ray beam is incident in the strip region C which is the second strip region from the strip region A. The FPD 4 detects the X-ray at the strip region C and then outputs the detection signal to the image generation element 21. Since a carrier remains in the amorphous selenium layer 31 of the strip region C right after output of the detection signal, the strip region C cannot be used for the next immediate shooting. Accordingly, the FPD 4 moves relative to the X-ray tube 3 along the movement direction of the X-ray tube (vertical direction) so that the X-ray incident region in the FPD 4 on shooting of the strip image T1 as to the region r1 relative to the X-ray tube 3 and the X-ray incident region in the FPD 4 on the next shooting of the strip image T2 shall not overlap. Further specifically, the FPD 4 relative to the X-ray tube 3 moves so that a radiation becomes incident in the different strip region every shooting of the strip image T. The strip image T is continuously taken in the rate of approximately 30 frames per second.

After that, the shootings of the region r3, r4, r5, r6 of the subject will be also conducted. The X-ray tube 3 and the FPD 4 keep moving every such shooting. The X-ray tube 3 moves to the incident position of the X-ray beam collimated to the shooting region of the subject M.

A movement of a FPD 4 is illustrated.

When the region r3 of the subject M is shot, the FPD 4 moves to the strip region E that is the incident position of the X-ray beam, which is 2 regions from the strip region C used for the shooting of the region r2 but the region A already used on the shooting of the region r1. (Referring to the upper right of FIG. 7).

Next, when the region r4 of the subject M is shot, the FDP 4 moves from the strip region E, used to shoot the region r3, to the adjacent strip region F which is the X-ray beam's incident position. (Referring to lower left of FIG. 7) Then, when the region r5 of the subject M is shot, the FDP 4 moves from the strip region F used to shoot the region r4 to the strip region D which is 2 regions up from the strip region F and is the X-ray beam's incident position. (Referring to the lower middle of FIG. 7).

Then, when the region r6 of the subject M is shot, the FDP 4 moves from the strip region D used to shoot the region r5 to the strip region B which is 2 regions up from the strip region D but the strip region F that is already used to shoot the region r4 and is the X-ray beam's incident position. (Referring to the lower right of FIG. 7).

Specifically, the strip region A of the FPD 4 is used for shooting the region r1 of the subject M, and then the strip region C, the strip region E, the strip region F, the strip region D, the strip region B is respectively used for shooting of the region r2, the region r3, the region r4, the region r5, the region r6. Accordingly, an unused strip region is always used on shooting each region of the subject M because the strip region to be shot is different every region of the subject M. The unused strip region is always used on shooting so that such shooting can be conducted under the condition in which no electric charge certainly remains in the amorphous selenium layer 31.

Figure 8:
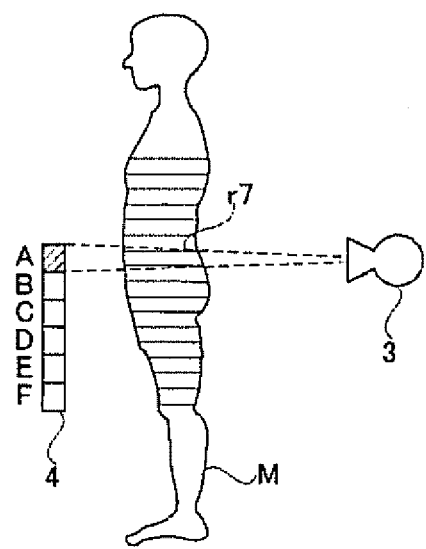
FIG. 8 is a pattern diagram illustrating an operation of a radiographic apparatus according to Embodiment 1.

After all strip images that the FPD 4 has are used, the strip region A that is used on the first shooting is used to shoot. Specifically, after the shooting using the strip region B, the FPD 4 moves to the strip region A which is adjacent to the strip region B and is the X-ray beam's incident position. (Referring to FIG. 8) The strip region A is used again for shooting under the time interval condition that is from the previous shooting until the time required for 5 shootings goes by. If it takes so much time until re-shooting, the electric charge occurred on the previous shooting no longer remains in the amorphous selenium layer 31 of the strip region A. Accordingly; the carrier remaining in the amorphous selenium layer 31 does not affect the shooting of the region r7 of the subject M. As well as described above, a strip region E, F, D, E is used in sequence to shoot the following region of the subject M. As the strip region at which the time goes by from the previous shooting until the time required for 5 shootings is used for each shooting, it is not affected by the remained eclectic charge.

Figure 9:
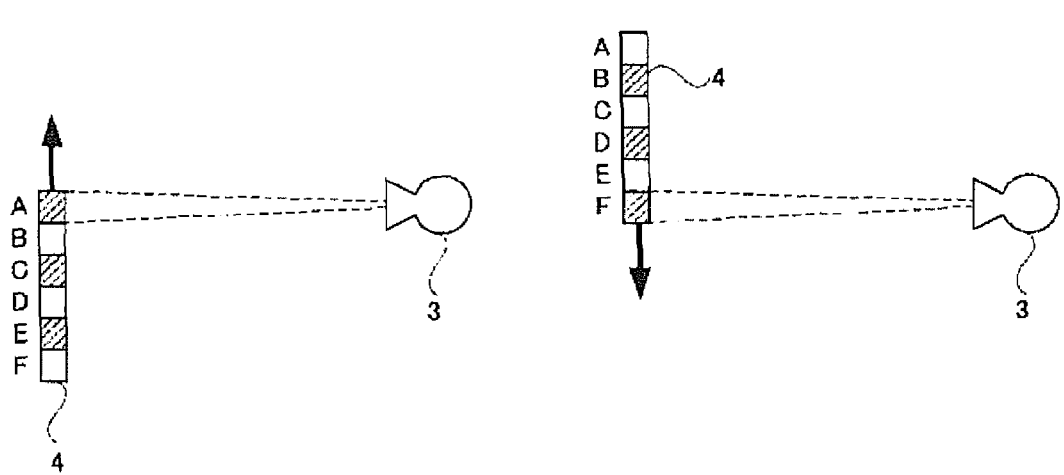
FIG. 9 is a pattern diagram illustrating an operation of a radiographic apparatus according to Embodiment 1.

Next, the reason why the strip region C is used instead of the region B following the shooting using the strip region A is illustrated. The shooting skipping the immediate adjacent strip region is conducted so that the movement process of the long distance as to the FPD 4 can be skipped. A relative position of the FPD 4 viewed from the X-ray tube 3 is illustrated in FIG. 9. The left side of FIG. 9 corresponds to the upper left of FIG. 7 and the X-ray tube 3 is relative to the upper end of the FPD 4. And, while the shooting proceeds, the FPD 4 moves upward vertically when it is viewed from the X-ray, as indicated by the arrow of the left side of FIG. 9. Then, the X-ray tube reaches to the lower end of the FPD 4. This state is shown at the right side of FIG. 9. When the shootings proceed further, the FPD 4 moves downward vertically when it is viewed from the X-ray, as indicated by the arrow of the right side of FIG. 9. In other words, along with ongoing shooting, the FPD 4 moves reciprocally relative to the X-ray tube 3.

During the reciprocal movement of the FPD 4, the strip region A, C, E is used outward for shooting and the strip region B, D, F is used homeward for shooting. (Referring to FIG. 9) Specifically, the strip region is distinguished between one used during outward movement of the FPD 4 relative to the X-ray tube 3 and one used during homeward movement of the FPD 4 relative to the X-ray tube 3. And further specifically, it is constituted so that the strip regions of the FPD 4 are alternatively arrayed corresponding to either onward use or homeward use. Accordingly, the FPD 4 shall move only the width of 2 strip regions relative to the X-ray tube 3 so that the above configuration can be achieved.

Given the strip region A-F is used according to the array sequence, the strip region A shall be used after the shooting of the strip region F that is located at the lower end. Because the electric charge likely remained in the amorphous selenium layer 31 can be in the state of satisfactory annihilation as the strip region A is used for the first shooting.

Figure 10:
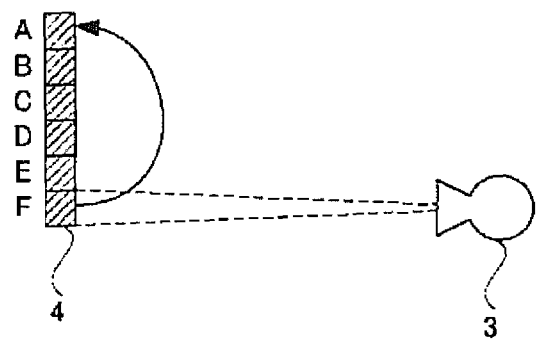
FIG. 10 is a pattern diagram illustrating an operation of a radiographic apparatus according to Embodiment 1.
Figure 11:
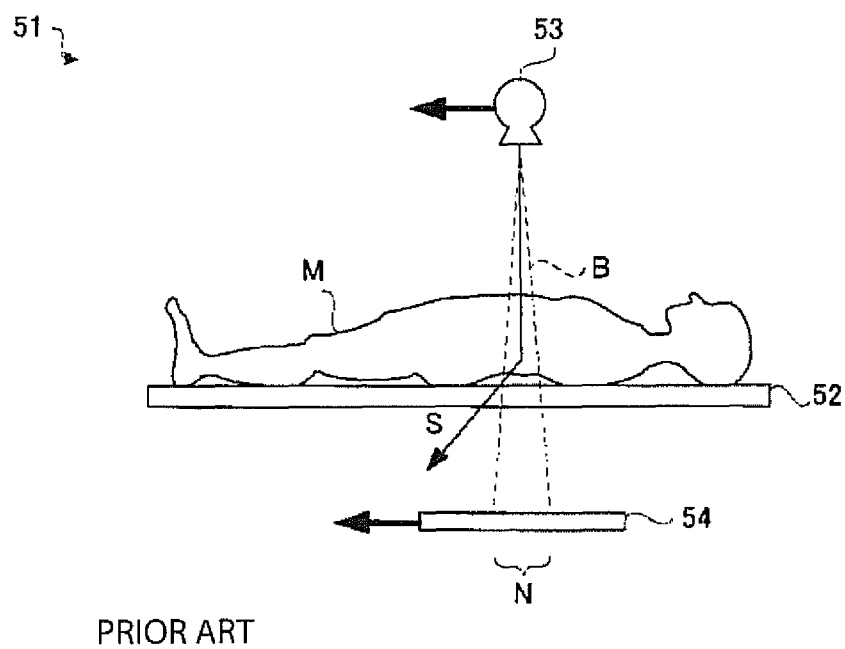
FIG. 11 is a pattern diagram illustrating a constitution of a conventional radiographic apparatus.
Figure 12:
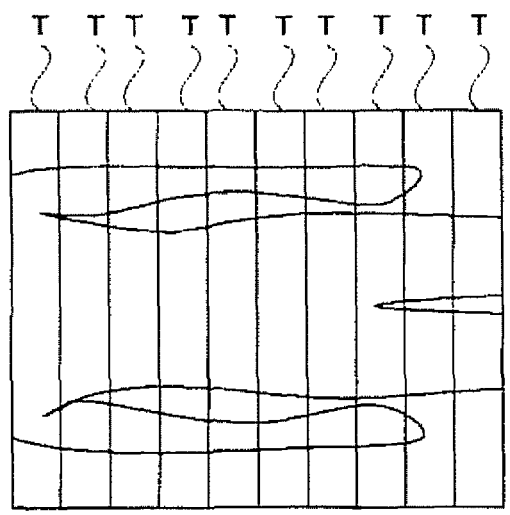
FIG. 12 is a pattern diagram illustrating an operation of a conventional radiographic apparatus.

Referring to FIG. 10, after shooting the strip region F at one end of the FPD 4, when the strip region A at the other end of the FPD 4 is used, the FPD 4 must move the long distance (distance corresponding to 4 strip regions) from the lower end to the upper end of the FPD 4 relative to the X-ray tube 3 in one time. Accordingly, an immediate shooting using the strip region A can be impossible after shooting using the strip region F, and the continuous shooting rate as to the regions of the subject M is suppressed. Then, the effect of the body movement of the subject M appears likely in a composite image. According to the constitution of Embodiment 1, such problem will not take place because a long distance movement of the FPFD 4 relative to the X-ray tube 3 is not mandatory.

Strip Image Generation Step S4

The detection signal which the FPD 4 outputs is sent to an operative image generation element 21. The image generation element 21 generates a rectangular strip image T in the direction of the sides of body of the subject M, in which a part of the subject M appears. The region r1 of the subject M appears in the strip image T1 that is taken at the first shooting, and the region r2 of the subject M, which is adjacent to the region r1, appears in the strip image T2 that is taken at the following shooting.

The strip image T1 which the image generation element 21 generates is sent to a composite image generation element 22. The composite image generation element 22 arrays and connects the strip images T in sequence of shootings in the direction of body axis of the subject M to generate a composite image PO. The composite image PO can be obtained by connecting the strip image T1 in the width direction, in which the latter half regions of the subject M appear. (Referring to FIG. 5) When this composite image PO is displayed on a display element 26, the examination is over.

As described above, according to the constitution of Embodiment 1, the constitution comprises a composite image generation element 21 to generate a single composite image PO by connecting the strip images T which are extending in the horizontal direction S orthogonal to the movement direction (vertical direction V) of the X-ray tube 3. Accordingly, a transmissive image of the subject M having an excellent visual recognition, in which the scattered radiation is erased, can be obtained. Then, according to the constitution of Embodiment 1, it is devised that the continuous shooting rate relative to strip images T can be increased. Specifically, a shooting is conducted, while the FPD 4 relative to the X-ray tube 3 is moving, so that a region of incident radiation in the FPD 4 on shooting a strip image T and a region of the following incident radiation in the FPD 4 on shooting a strip image T do not overlap. Once an X-ray is irradiated to the FPD 4, the irradiated part cannot be used for an immediate shooting. Then, according to the constitution of Embodiment 1, continuous shootings can be conducted while the FPD 4 relative to the X-ray tube is moving. Accordingly, since the shooting the strip image T as to the FPD 4 is conducted by using an unused part, the time between shootings can be cut and then the shooting can be completed before the subject moves the body. Accordingly, when the composite image PO is generated, the subject's image appearing in each strip image T can be connected without misalignment with each other so that a transmissive image having an excellent visual recognition can be obtained.

In addition, according to the above constitution, a composite image PO is generated by connecting plural strip images T. Such strip image T is taken by using any one of the strip regions T of the FPD 4. According to this manner, it is possible for parts of the FPD 4 used on shooting each strip image T certainly not to overlap.

In addition, according to the above constitution, the rate of continuous shooting can be further increased. If the continuous shooting of the strip image T can be conducted by moving the FPD 4 relative to the X-ray tube 3 to the other end in the reverse direction of the previous movement after shooting the strip region positioned at one end of the FPD 4 is conducted, the shooting can be conducted continuously without waiting until the strip region at one end of the FPD 4 becomes ready for shooting.

According to the above constitution, the strip region for the outward use is used to shoot a strip image T while the FPD 4 moves forward from the one end to the other end (when the movement of the FPD 4 is outward) under the reciprocal movement of the FPD 4 relative to the X-ray tube 3 on obtaining the strip image T. Also, according to the above constitution, the strip region for the homeward use is used to shoot a strip image T while the FPD 4 moves forward from the other end to the one end (when the movement of the FPD 4 is homeward.) Given the same strip region on outward and homeward shootings is used, this strip region must be used twice within one reciprocal movement of the FPD 4 relative to the X-ray tube 3. Then, in some cases, the time between shootings is too short, and therefore, the waiting time until the strip region becomes ready to use emerges. According to the above constitution, the strip region is only used once during the reciprocal movement of the FPD 4 relative to the X-ray tube 3 so that the shooting of the strip region can be continuously conducted without setting a waiting time.

In accordance with the above constitution, a strip region for outward use and a strip region for homeward use are arrayed one after the other so that the effect of the present invention can be achieved only by moving the FPD 4 relative to the X-ray tube 3 by skipping one strip. The moving distance of the FPD 4 relative to the X-ray tube 3 is relatively short so that the continuous shooting rate of the strip image T can be further increased.

In addition, when all strip regions are used to shoot the strip image T, the strip region used at the first shooting, i.e. the longest time passed from the shooting, will be used so that the immediate shooting of the strip image T can be conducted without setting a waiting time because the time interval between the previous shooting and the following shooting using the instant strip region is satisfactorily long.

In addition, an amorphous selenium layer 31 to convert an X-ray to an electric charge has a characteristic by which a complete annihilation of emerged electric charge takes a time. A constitution of the present invention is suitable to a constitution comprising a FPD 4 having such amorphous selenium layer 31.

The present invention is not limited to the above constitution and methods therefore and may work in the following alternative exemplary manners without limitation thereto.

(1) The above Embodiment is related to a medical device but also can be applied to an industrial device and a nuclear device.

(2) An X-ray in the above Embodiment is one example of radiations. Accordingly, the present invention is applicable to other radiations than an X-ray.

(3) The above Embodiment is related to a shooting apparatus for a subject in a standing position, but it can be a shooting apparatus for a subject in a dorsal position, which has a table on which a subject is loaded or in any other operatively suitable position and is not limited thereto.

(4) According to the above Embodiment, a strip region A is used for shooting of the first strip image T, but the present invention is not limited to this aspect and the other strip region can be used for shooting of the first strip image T.

EXPLANATION OF REFERENCES

T: Strip image
3: X-ray tube (radiation source)
4: FPD (Detection means)
11: X-ray tube movement mechanism (Radiation source movement mechanism)
12: X-ray tube movement control element (Radiation source movement control means)
15: FPD movement mechanism (detector movement means)
16: FPD movement control element (detector movement control means)
21: Image generation element (image generation means)
22: Composite image generation means (composite image generation means)
31: Amorphous selenium layer (conversion layer)

It will be understood by those of skill in the art that the use of the phrases constitute, constitution, comprising, exemplary, embodiment, illustration, step, or system are provided as assistive aids to the reader and are not used to imply a required limiting arrangement or structure or assembly of features or aspects or functions or method steps to the invention. The aspects of the invention as discussed herein are to be considered broadly and without limitation. For example, the above method steps may be modified for use during operation of the apparatus and systems proposed, such that multiple methods of operating the same may be readily accommodated without departing from the scope and spirit of the proposed invention. It will be further understood by those of skill in the art that the use of the phrase means may be interchangeably used with the phrase element, system, or feature, to be operably understood by those of suitable skill. Thus, that the feature, aspect, means, or element will be as described and function as enabled or described within the skill of one of the art.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure covers modifications and variation of this invention provided they come within the scope of the appended claims and their equivalents.

What is claimed is:

1. A radiographic apparatus, comprising:
    a radiation source operative to irradiate a radiation;
    a radiation source movement means operative to move said radiation source during a use thereof;
    a radiation source movement control means to control said radiation source movement means during said use;
    a detection means operative to detect a irradiated radiation and to output a detection signal;
    a detector movement means operative to move said detection means;
    a detector movement control means operative to control said detector movement means;
    an image generation means operative to generate a strip image extending to a direction orthogonal to a movement direction of said radiation source from a detection signal, wherein a shooting is operatively conducted in sequence with an incident radiation in a part of a detection means while said radiation source relative to a subject is moving;
    a composite image generation means operative to generate a single composite image by operatively connecting said strip images, wherein said image generation means outputs, in the movement direction of said radiation source during said use; and wherein as an operative a shooting is conducted while said detection means keeps moving relative to said radiation source in the movement direction of said radiation source so that an incident radiation region in said detection means on a previous shooting said strip image and an incident radiation region in said detection means on a following shooting said strip image do not overlap.

2. A radiographic apparatus, according to claim 1, wherein:
an incident radiation region in said detection means on shooting said strip image is a strip region extending in a direction orthogonal to a movement direction of said radiation source; said strip region arrays in a movement direction of said radiation source in said detection means; and
said detection movement control means moves said detection means so that an incident radiation strip region can be different every shooting of said strip image.

3. A radiographic apparatus, according to claim 2, wherein:
said detector movement control means provides said detection means relative to said radiation source with a reciprocal movement on shooting said strip image.

4. A radiographic apparatus, according to claim 3, wherein:
said strip region used during outward movement of said detection means relative to said radiation source is different from said strip region used during a homeward movement of said detection means relative to said radiation source.

5. A radiographic apparatus, according to claim 4, wherein:
a strip region for outward use and a strip region for homeward use are arrayed one after the other in said detection means.

6. A radiographic apparatus, according to claim 2, comprising:
a step of said detector movement control means moves said detection means so that an unused strip region can be used for shooting during shooting said strip image, and a step of said detector movement control means moves said detection means so that a strip region used for the first shooting can be used for shooting when all strip regions are used.

7. A radiographic apparatus, according to claim 5, comprising:
a step of said detector movement control means moves said detection means so that an unused strip region can be used for shooting during shooting said strip image, and a step of said detector movement control means moves said detection means so that a strip region used for the first shooting can be used for shooting when all strip regions are used.

8. A radiographic apparatus, according to claim 2, further comprising:
a collimator that collimates a radiation beam irradiated from said radiation source and operative to irradiate all said strip regions of said detection means.

9. A radiographic apparatus, according to claim 6, further comprising:
a collimator that collimates a radiation beam irradiated from said radiation source and operative to irradiate all said strip regions of said detection means.

10. A radiographic apparatus, according to claim 2, wherein:
said detection means further comprises a conversion layer to convert a radiation to an electric charge.

11. A radiographic apparatus, according to claim 9, wherein:
said detection means further comprises a conversion layer to convert a radiation to an electric charge.

12. A method for operating a radiographic apparatus, comprising the steps of:
providing a radiation source operative to irradiate a radiation;
operating a radiation source movement means to move said radiation source during a use thereof;
controlling a radiation source movement control to control said radiation source movement means during said use;
operating a detection means to detect a irradiated radiation and to output a detection signal;
operating a detector movement means to move said detection means;
operating a detector movement control means to control said detector movement means;
providing an image generation means and operating said image generation means operative to generate a strip image extending to a direction orthogonal to a movement direction of said radiation source from a detection signal, wherein a step of shooting is operatively conducted in sequence with an incident radiation in a part of a detection means while said radiation source relative to a subject is moving;
generating a single composite image by operating a composite image generation means to generate a single composite image by operatively connecting said strip images, wherein said image generation means outputs, in the movement direction of said radiation source, during said use; and
conducting a shooting while said detection means keeps moving relative to said radiation source in the movement direction of said radiation source so that an incident radiation region in said detection means on a previous shooting said strip image and an incident radiation region in said detection means on a following shooting said strip image do not overlap.

13. A method, according to claim 12, wherein:
an incident radiation region in said detection means on shooting said strip image is a strip region extending in a direction orthogonal to a movement direction of said radiation source; said strip region arrays in a movement direction of said radiation source in said detection means; and
said method farther conducts a step of operating said detection movement control means and moving said detection means so that an incident radiation strip region can be different every shooting of said strip image.

14. A method, according to claim 13, further comprising the step of:
providing said detector movement control means and operating said detection means relative to said radiation source with a reciprocal movement on shooting said strip image.

15. A method, according to claim 14, further comprising the step of:
operating said apparatus whereby said strip region used during outward movement of said detection means relative to said radiation source is different from said strip region used during a homeward movement of said detection means relative to said radiation source.

16. A method, according to claim 14, wherein:
a strip region for outward use and a strip region for homeward use are arrayed one after the other in said detection means.

17. A method, according to claim 13, further comprising the step of:
operating said detector movement control means and moving said detection means so that an unused strip region can be used for shooting during shooting said strip image, and said detector movement control means moving said detection means so that a strip region used for the first shooting can be used for shooting when all strip regions are used.

18. A method, according to claim 16, further comprising the step of:

operating said detector movement control means and moving said detection means so that an unused strip region can be used for shooting during shooting said strip image, and said detector movement control means moving said detection means so that a strip region used for the first shooting can be used for shooting when all strip regions are used.

19. A method, according to claim 13, further comprising the step of:

collimating, with a collimator a radiation beam irradiated from said radiation source and irradiating all said strip regions of said detection means.

20. A method, according to claim 17, further comprising the step of:

providing a conversion layer in said detection means; and converting via said conversion layer a radiation to an electric charge.

* * * * *